United States Patent
Youn et al.

(10) Patent No.: US 9,179,877 B2
(45) Date of Patent: Nov. 10, 2015

(54) MEDICAL IMAGING APPARATUS AND METHOD OF PROVIDING OPERATIONAL INFORMATION OF GANTRY INCLUDED IN THE SAME

(71) Applicant: SAMSUNG ELECTRONICS CO., LTD., Suwon-si (KR)

(72) Inventors: Eung-jun Youn, Wonju-si (KR); Byung-sun Choi, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 72 days.

(21) Appl. No.: 13/937,886

(22) Filed: Jul. 9, 2013

(65) Prior Publication Data
US 2014/0119494 A1 May 1, 2014

(30) Foreign Application Priority Data
Nov. 1, 2012 (KR) ........................ 10-2012-0123099

(51) Int. Cl.
*A61B 6/03* (2006.01)
*A61B 6/00* (2006.01)

(52) U.S. Cl.
CPC . *A61B 6/032* (2013.01); *A61B 6/44* (2013.01); *A61B 6/465* (2013.01)

(58) Field of Classification Search
CPC .................... A61B 6/032; A61B 6/461–6/466; A61B 6/44
USPC .......................................................... 378/98
See application file for complete search history.

(56) References Cited

U.S. PATENT DOCUMENTS

| | | | |
|---|---|---|---|
| 6,590,960 B2 | 7/2003 | Kroener et al. | |
| 7,358,479 B2 | 4/2008 | Welker | |
| 7,869,859 B2 * | 1/2011 | Shinno et al. | 600/425 |
| 7,933,376 B2 | 4/2011 | Yoda et al. | |
| 7,991,115 B2 | 8/2011 | Matsuzawa et al. | |
| 2005/0027197 A1 | 2/2005 | Segawa et al. | |
| 2008/0204017 A1 | 8/2008 | Takamori et al. | |
| 2009/0016486 A1 * | 1/2009 | Brown | 378/42 |
| 2009/0154647 A1 | 6/2009 | Matsuzawa et al. | |
| 2010/0215141 A1 * | 8/2010 | Kondo et al. | 378/16 |

FOREIGN PATENT DOCUMENTS

| | | |
|---|---|---|
| CN | 1371662 | 10/2002 |
| CN | 1572235 | 2/2005 |
| CN | 101455572 | 6/2009 |

(Continued)

OTHER PUBLICATIONS

Korean Office Action issued May 23, 2014 in corresponding Korean Patent Application No. 10-2012-0123099.

(Continued)

*Primary Examiner* — Glen Kao
*Assistant Examiner* — Dani Fox
(74) *Attorney, Agent, or Firm* — Staas & Halsey LLP (57) ABSTRACT

A medical imaging apparatus and/or method includes a gantry, a control unit, and a display unit. The gantry has a source for generating an X-ray and a detector for detecting the X-ray passing through an object. The gantry allows the source and the detector to rotate around the object. The control unit obtains operational information of the gantry. The display unit outputs the obtained operational information of the gantry.

22 Claims, 7 Drawing Sheets

(56) References Cited

FOREIGN PATENT DOCUMENTS

| | | |
|---|---|---|
| CN | 202408929 | 9/2012 |
| JP | 9-192123 | 7/1997 |
| JP | 2007-7255 | 1/2007 |
| JP | 2008-149118 | 7/2008 |
| JP | 2009-160390 | 7/2009 |
| JP | 2010-194358 | 9/2010 |
| KR | 1999-0071158 | 9/1999 |

OTHER PUBLICATIONS

Korean Office Action mailed Nov. 21, 2013 in corresponding Korean Application No. 10-2012-0123099.
Korean Notice of Final Rejection dated Nov. 13, 2014 in corresponding Korean Patent Application No. 10-2012-0123099.
Korean Notice of Final Rejection Reexamination dated Jan. 8, 2015 in corresponding Korean Patent Application No. 10-2012-0123099.
Chinese Office Action mailed May 13, 2015 in corresponding Chinese Application No. 201310534853.9.

* cited by examiner

MEDICAL IMAGING APPARATUS AND METHOD OF PROVIDING OPERATIONAL INFORMATION OF GANTRY INCLUDED IN THE SAME

CROSS-REFERENCE TO RELATED APPLICATIONS

This application claims the benefit of Korean Patent Application No. 10-2012-0123099, filed on Nov. 1, 2012, in the Korean Intellectual Property Office, the disclosure of which is incorporated herein in its entirety by reference.

BACKGROUND

1. Field

The present invention relates to a medical imaging apparatus and a method of providing operational information of a gantry included in the medical imaging apparatus.

2. Description of the Related Art

A computerized tomography (CT) imaging apparatus processes data regarding a shape of an internal section of an object to obtain an image by projecting an X-ray toward the object at various angles and reconfiguring the projected X-rays by using a computer.

The CT imaging apparatus having a roughly donut shape includes an apparatus for accommodating a patient at the center thereof, which is generally referred to as a gantry. An X-ray source and a detector for detecting the X-ray are mounted on the donut shaped gantry. An opening of the gantry is disposed between the X-ray source and the detector. When an object is to be scanned so as to form an image thereof, the object is laid on a transfer device and is carried through the opening of the gantry. Then, the CT imaging apparatus operates the X-ray source and detector of the gantry so as to rotate them, operates the X-ray source to generate an X-ray, and operates the detector to detect the X-ray that has passed through the object. The CT imaging apparatus receives a signal corresponding to an intensity of the X-ray acquired from the gantry and generates an image according to an X-ray attenuation factor in a sectional plane of the object by calculating the received signal.

SUMMARY

Additional aspects and/or advantages will be set forth in part in the description which follows and, in part, will be apparent from the description, or may be learned by practice of the invention.

The present invention provides a medical imaging apparatus that facilitates checking operational information of a gantry from the outside.

The present invention provides a method of providing operational information of a gantry included in the medical imaging apparatus.

According to an aspect of the present invention, a medical imaging apparatus including a gantry including a source for generating an X-ray and a detector for detecting the X-ray passing through an object, wherein the gantry allows the source and the detector to rotate around the object, a control unit for obtaining operational information of the gantry, and a display unit for outputting the obtained operational information of the gantry.

The operational information of the gantry may include at least one of scanning operation information indicating whether the gantry is performing a scanning operation, rotational information regarding at least one of the source and the detector, malfunction information indicating whether the gantry is operating normally, and positional information regarding at least one of the source and the detector in the gantry.

The rotational information may include at least one of a rotational speed and a rotational direction.

The display unit may include a first display unit for outputting the operational information of the gantry by using light emitting diodes (LEDs). The first display unit may include an LED display that is circularly provided on an outer surface of the gantry. The first display unit may indicate the operational information of the gantry by changing colors of the LEDs.

The display unit may include a second display unit for outputting the operational information in an image. The second display unit may display the operational information on an image of the gantry. The second display unit may display rotational information regarding at least one of the source and the detector on the image of the gantry by using an arrow.

The second display unit may display scanning operation information of the gantry on the image of the gantry by using colors. The second display unit may further output a computerized tomography (CT) image of the object and a body marker corresponding to the CT image of the object.

According to another aspect of the present invention, a method of providing operational information of a gantry included in a medical imaging apparatus includes driving the gantry to allow a source and a detector included in the gantry to rotate around an object, obtaining the operational information of the gantry, and displaying the obtained operational information of the gantry.

The displaying of the obtained operational information of the gantry may include outputting the operational information of the gantry by using LEDs. The outputting of the operational information of the gantry by using the LEDs may include outputting the operational information of the gantry by using an LED display that is circularly provided on an outer surface of the gantry.

The displaying of the obtained operational information of the gantry may include outputting the operational information as an image. The outputting of the operational information in the image may include displaying the operational information on an image of the gantry.

According to another aspect of the present invention, a medical imaging apparatus for obtaining a medical image from a predetermined signal passing through an object includes a gantry including a source for generating the signal and a detector for detecting the signal passing through an object, wherein the gantry allows the source and the detector to rotate around the object, a control unit for obtaining malfunction information of the gantry, and a display unit for outputting the obtained malfunction information of the gantry.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION

The attached drawings for illustrating exemplary embodiments of the present invention are referred to in order to gain a sufficient understanding of the present invention, the merits thereof, and the objectives accomplished by the implementation of the present invention. Hereinafter, the present invention will be described in detail by explaining exemplary embodiments thereof with reference to the attached drawings. Like reference numerals in the drawings denote like elements.

As used herein, the term "and/or" includes any and all combinations of one or more of the associated listed items. Expressions such as "at least one of," when preceding a list of elements, modify the entire list of elements and do not modify the individual elements of the list.

The present invention will now be described more fully with reference to the accompanying drawings, in which exemplary embodiments of the invention are shown. In the following description, when detailed descriptions about related well-known functions or structures are deemed to unnecessarily obscure the essence of the present invention, the detailed descriptions will be omitted.

When a part "includes" a certain constituent element, unless specified otherwise, it may not be construed to exclude another constituent element but may be construed to further include other constituent elements. The terms such as "~ portion", "~ unit", "~ module", and "~ block" stated in the specification may signify a unit to process at least one function or operation and the unit may be embodied by hardware, software, or a combination of hardware and software. Also, as a computer software command to embody the present invention, hardware, software, or a combination of hardware and software may be used instead of a programmed processor/controller. Accordingly, the present invention is not limited by a specific combination of hardware and software.

Throughout the specification, an "object" may refer to a part of a human body. For example, the object may include organs such as liver, heart, womb, breasts, and stomach, or a fetus, or any one section of a human body. Also, a "user" may be a medical expert, for example, a medical doctor, a nurse, a clinical pathologist, or a medical image expert, but the present invention is not limited thereto.

Figure 1A:
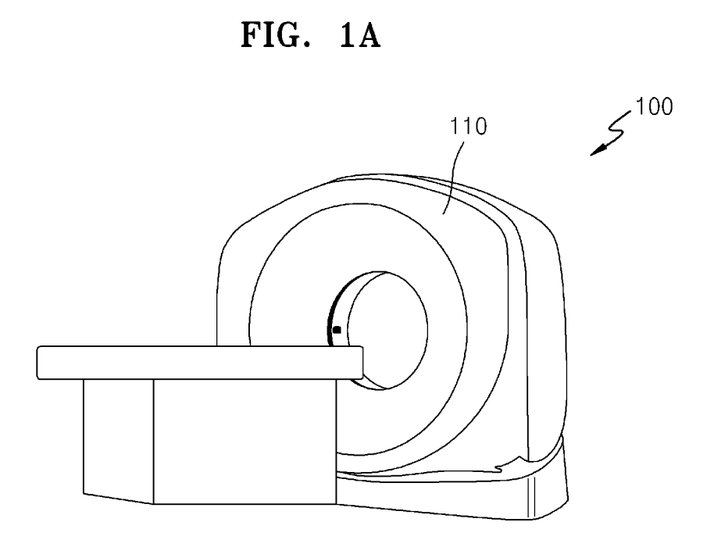
FIGS. 1A and 1B schematically illustrate a general computerized tomography (CT) imaging apparatus.
Figure 1B:
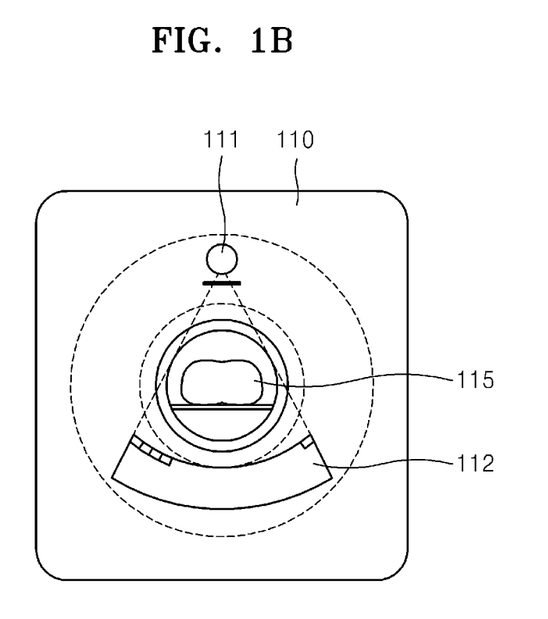

FIGS. 1A and 1B schematically illustrate a general computerized tomography (CT) imaging apparatus 100. Referring to FIG. 1A, the general CT imaging apparatus 100 denotes an apparatus for obtaining a medical image with respect to an object by using an X-ray. The general CT imaging apparatus 100 may include a gantry 110. The gantry 110 may have a donut shape so as to accommodate an object in an opening portion thereof.

As illustrated in FIG. 1B, the gantry 110 may include a source 111 for irradiating an X-ray toward an object 115 and a detector 112 for detecting the x-ray passing through the object 115. The source 111 and the detector 112 included in the gantry 110 may be rotated by 360° around the object 115 to obtain image data of the object 115. In the case of the general CT imaging apparatus 100, however, since the exterior of the gantry 110 is covered by a case, it is difficult for a user to identify positions of major parts, for example, the source 111 and the detector 112, existing inside the gantry 110.

The present invention enables a user to easily identify operational information of a medical imaging apparatus or a part included in the medical imaging apparatus. The present invention may be widely applied to a medical imaging apparatus such as a magnetic resonance imaging (MRI) apparatus, a positron emission tomography (PET) apparatus, or an ultrasonic wave imaging apparatus, in addition to a medical CT imaging apparatus.

Figure 2:
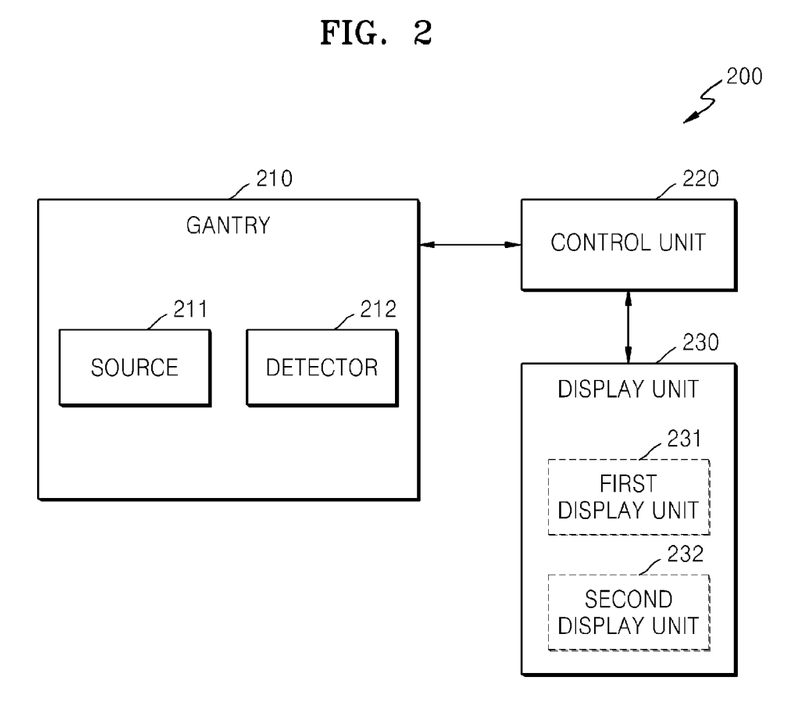
FIG. 2 is a block diagram of a medical imaging apparatus according to an embodiment of the present invention.

FIG. 2 is a block diagram of a medical imaging apparatus 200 according to an embodiment of the present invention. Referring to FIG. 2, the medical imaging apparatus 200 may include a gantry 210, a control unit 220, and a display unit 230. However, not all of the elements illustrated in FIG. 2 are essential elements. The medical imaging apparatus 200 may be embodied by more or less elements than illustrated in FIG. 2. The above-mentioned elements are described below.

The gantry 210 may include therein a source 211 for generating a predetermined signal and a detector 212 for detecting a signal passing through an object. The gantry 210 may rotate the source 211 and the detector 212. For example, the signal may be an X-ray signal, an MR signal, or an ultrasonic wave signal. It is understood that the signal is not limited to X-ray signal.

The control unit 220 typically controls an overall operation of the medical imaging apparatus 200. For example, the control unit 220 may generally control the gantry 210 or the display unit 230 by executing programs stored in a memory (not shown). Also, the control unit 220 may obtain operational information of the gantry 210.

The control unit 220 may obtain operational information of the gantry 210 from the gantry 210 and transmit the obtained information to the display unit 230. The display unit 230 outputs (displays) information processed in the medical imaging apparatus 200. For example, the display unit 230 may output the operational information of the gantry 210 obtained from the control unit 220.

The display unit 230 may include a first display unit 231 and/or a second display unit 232. The display unit 230 may further include sound output unit.

The first display unit 231 may output the operational information of the gantry 210 by using a light emitting diode (LED). However, the display unit 230 may have LCD display unit. Further, the display unit 230 may have OLED display unit. According to the present embodiment, the first display unit 231 may be an LED display that is provided on an outer surface of the gantry 210 and has a circular shape. The first display unit 231 may be configured to output the operational information of the gantry 210 by circularly arranging LEDs around the gantry 210 and entirely or partially changing the colors of the LEDs.

The second display unit 232 may output the operational information of the gantry 210 in a form of an image. For example, the second display unit 232 may display the operational information of the gantry 210 on an image of the gantry 210.

A method of providing the operational information of the gantry 210 by using the respective elements of the medical imaging apparatus 200 is described below with respect to FIG. 3.

Figure 3:
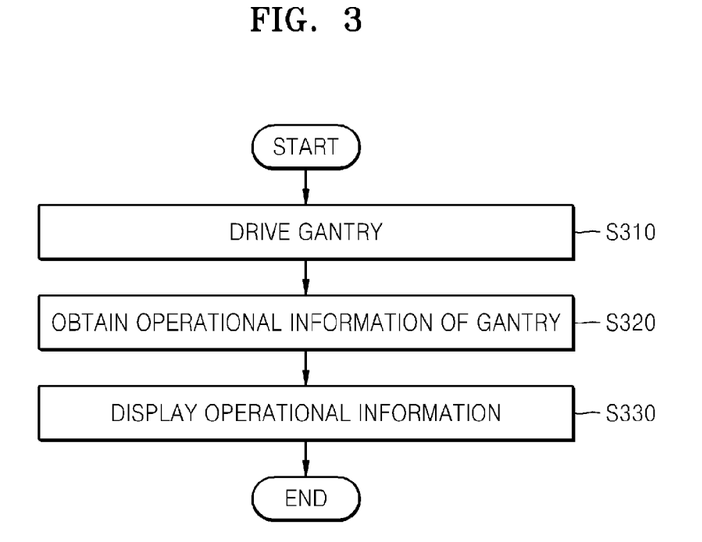
FIG. 3 is a flowchart for explaining a method of providing operational information of a gantry, according to an embodiment of the present invention.

FIG. 3 is a flowchart for explaining a method of providing operational information of a gantry, according to an embodiment of the present invention.

Referring to FIG. 3, the method of providing operational information of a gantry according to the present embodiment may include operations that are processed in the medical imaging apparatus 200 of FIG. 2. Accordingly, it may be seen that the above descriptions of the medical imaging apparatus 200 of FIG. 2 that may be omitted below are applied to the method of providing operational information of a gantry of FIG. 3.

In S310, the medical imaging apparatus 200 may drive the gantry 210 to rotate the source 211 and the detector 212 included in the gantry 210 around an object. The medical imaging apparatus 200 according to the present embodiment may control a rotational speed or a rotational direction of the source 211 and the detector 212. The operation of S310 may be performed by the control unit 220.

In S320, the medical imaging apparatus 200 may obtain the operational information of the gantry 210. The operational information of the gantry 210 according to the present embodiment may include image scanning operation information that indicates whether the gantry 210 is in a scanning operation. The scanning operation may include a scanning preparation operation, a scanning standby operation, a scanning-on operation, and a scanning stop operation. In other words, the scanning operation information may include information about not only whether the gantry 210 is performing the scanning operation, but also whether the gantry 210 is in a scanning standby state or a scanning preparation state.

The operational information of the gantry 210 may include rotational information of at least one of the source 211 and the detector 212. The rotational information may be information indicating, for example, a rotational speed or a rotational direction.

Also, the operational information of the gantry 210 may include malfunction information indicating whether the gantry 210 is normally operated. The malfunction information may indicate, for example, whether the source 211 and the detector 212 are aligned with each other or whether parts included in the gantry 210 are operating normally. The operational information of the gantry 210 according to the present embodiment may include positional information indicating where the parts included in the gantry 210, for example, the source 211 and the detector 212, are located in the gantry 210.

In S330, the medical imaging apparatus 200 may display the operational information of the gantry 210 obtained by the control unit 220. Thus, since the medical imaging apparatus 200 according to the present embodiment displays the operational information of the gantry 210 obtained by the control unit 220, an external user may receive the operational information of the gantry 210. As the user is provided with the operational information of the gantry 210, the user may easily check whether the gantry 210 malfunctions. For example, a user who is provided with the positional information of the source 211 and the detector 212 may quickly check whether the source 211 and the detector 212 are appropriately aligned with each other.

According to the present embodiment, the medical imaging apparatus 200 may output the operational information of the gantry 210 by using LEDs. In other words, the medical imaging apparatus 200 according to the present embodiment may indicate the operational information by changing the colors of the LEDs. For example, in order to indicate where the source 211 and the detector 212 are located in the gantry 210, the medical imaging apparatus 200 may display the operational information of the gantry 210 by dividing the LEDs into an LED for the position of the source 211, an LED for the position of the detector 212, etc. and changing the color and/or brightness of each LED.

Also, the medical imaging apparatus 200 according to the present embodiment may indicate malfunction information of the gantry 210 by lighting all of the LEDs or some of them, or changing the color thereof. For example, a part of the gantry 210 that does not work normally may be indicated by changing the color of an LED corresponding to that part.

In other words, according to the present embodiment, the LEDs that output the operational information of the gantry 210 may be used as an intuitive indicator of the operational state of the gantry 210. Also, the LEDs circularly provided on an outer surface of the gantry 210 may function as an indication lamp indicating the position of the source 211 or an X-ray tube and/or an indication lamp indicating the state of the gantry 210, for example, a scanning standby state or an X-ray image scanning-on state. In addition, the changeable colors of the LEDs may add an aesthetic function to enrich the external appearance of the gantry 210. The method of outputting the operational information of the gantry 210 by using the LEDs will be described in detail later with reference to FIG. 4.

The medical imaging apparatus 200 according to another embodiment of the present invention may output the operational information of the gantry 210 in a format of an image or sound. The operational information may be output in an image by being displayed on an image of the medical imaging apparatus 200 or on another image. For example, the operational information of the gantry 210 may be output as an image by being displayed on an image of the gantry 210.

The medical imaging apparatus 200 may display the operational information of the gantry 210 by using any one of predetermined colors, shapes, and signs. For example, the medical imaging apparatus 200 may display on an image of the gantry 210 the rotational information of at least one of the source 211 and the detector 212 provided in the gantry 210 by using an arrow shape or a finger shape. In detail, a rotational speed or a rotational direction of the source 211 or the detector 212 may be indicated by the direction, position, thickness, brightness, or length of an arrow. In another example, the medical imaging apparatus 200 may indicate the state of the gantry 210 on an image of the gantry 210 by using a sign such as "X" for a scanning standby state, "Δ" for a scanning preparation state, and "O" for a scanning-on state. In another example, the medical imaging apparatus 200 may indicate on an image of the gantry 210 whether the gantry 210 is operating normally. In detail, malfunction information of the gantry 210 may be indicated by changing the color of a portion on the image of the gantry 210 corresponding to a part of the gantry 210 that malfunctions.

Thus, the medical imaging apparatus 200 according to the present embodiment may identify the operational information of the gantry 210 in real time a user checks an image. The method of outputting the operational information of the gantry 210 by using an image will be described in detail later with reference to FIG. 5.

The medical imaging apparatus 200 may output information other than the operational information of the gantry 210. For example, the medical imaging apparatus 200 may further output information about a direction in which an object is arranged, for example, whether a patient enters the gantry 200 head or feet first, or information of an object, for example, an ID to identify an object. Also, the medical imaging apparatus 200 may further output diagnosis result information indicating a past/present diagnosis result, a diagnosis date, and the combinations thereof.

According to the present embodiment, the medical imaging apparatus 200 may output a CT image of an object and a body marker corresponding to the CT image of the object. When a human body, for example, is CT-scanned, the body marker corresponding to the CT image of the object signifies a marker indicating a part of the human body corresponding to the scanned image.

The medical imaging apparatus 200 may receive the body marker from a user who scans the CT image of the object or may extract the body marker from object CT image information. As the medical imaging apparatus 200 displays a body marker indicating a scanned portion on the CT image, a user may quickly identify the scanned portion while viewing the CT image of the object. Also, when a user checks the CT image later, the scanned portion may be easily identified from the CT image. A method of outputting an image of an object and a body marker corresponding to the image of the object will be described in detail later with reference to FIG. 6.

FIGS. 4A to 4D schematically illustrate the first display unit 231 of the medical imaging apparatus, according to an embodiment of the present invention. Referring to FIGS. 4A to 4D, the first display unit 231 for outputting the operational information of the gantry 210 by using LEDs may be an LED display that is circularly provided on an outer surface of the gantry 210. The first display unit 231 in FIGS. 4A to 4D is configured to be able to change the color of all or some of the LEDs.

Figure 4A:
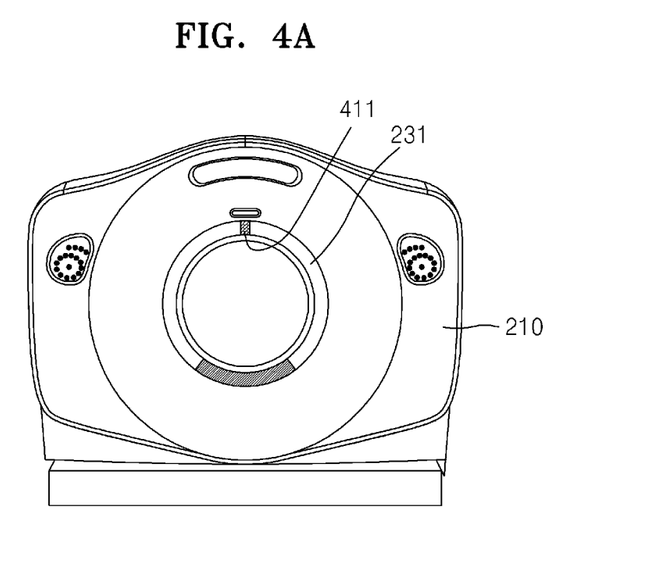
FIGS. 4A to 4D schematically illustrate a first display unit of the medical imaging apparatus, according to an embodiment of the present invention.
Figure 4B:
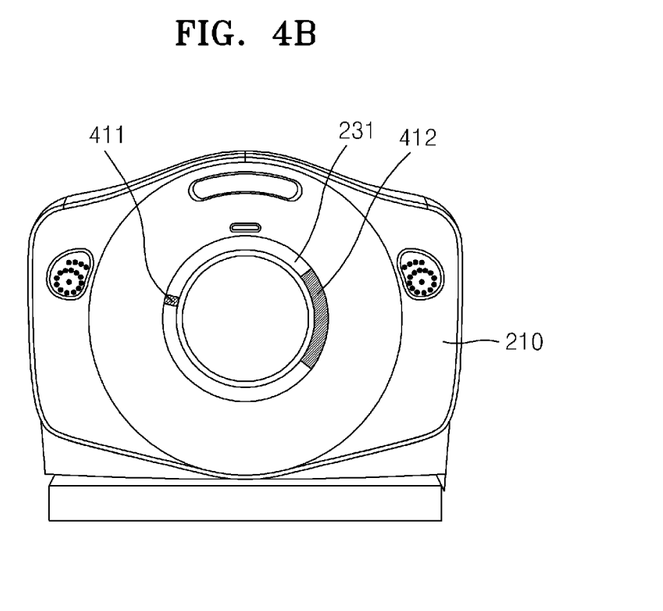

FIGS. 4A and 4B indicate that the gantry 210 of the medical imaging apparatus 200 is in a scanning standby state.

When the gantry 210 is in a scanning standby state, the medical imaging apparatus 200 may light the first display unit 231 in white. Also, the medical imaging apparatus 200 may light a portion 411 corresponding to the position of the source 211 in red and a portion 412 corresponding to the position of the detector 212 in yellow, in the first display unit 231.

As illustrated in FIG. 4B, after the gantry 210 in the scanning standby state performs a scanning operation and thus the source 211 and the detector 212 are rotated a predetermined distance counterclockwise, the gantry 210 may be returned to the scanning standby state. The first display unit 231 may display the positions of the source 211 and the detector 212 after moving, by using the LEDs.

Figure 4C:
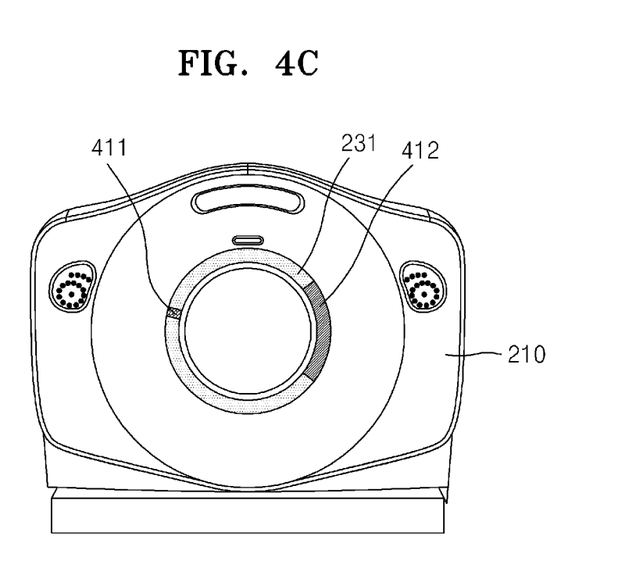

FIG. 4C illustrates that the gantry 210 is in a scanning preparation state. When the gantry 210 is in a scanning preparation state, the medical imaging apparatus 200 may light the first display unit 231 in green. Also, the portion 411 of the first display unit 231 corresponding to the position of the source 211 may be lit in black, whereas the portion 412 of the first display unit 231 corresponding to the position of the detector 212 may be lit in dark green.

Figure 4D:
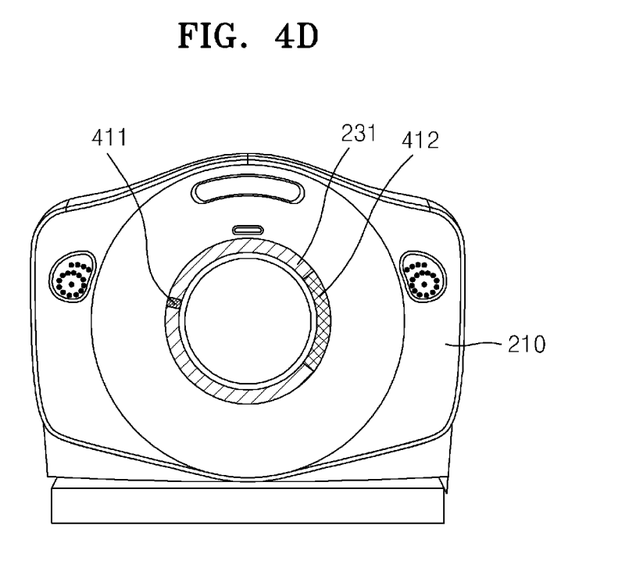

FIG. 4D illustrates that the gantry 210 is in a scanning-on state. When the gantry 210 is in a scanning-on state, the medical imaging apparatus 200 may light the first display unit 231 in red. Also, the portion 411 of the first display unit 231 corresponding to the position of the source 211 may be lit in black, whereas the portion 412 of the first display unit 231 corresponding to the position of the detector 212 may be lit in dark red.

FIGS. 5A to 5D schematically illustrate the second display unit 232 graphically displaying the operational information of the gantry 210 of the medical imaging apparatus 200, according to an embodiment of the present invention. As illustrated in FIG. 5, according to the present embodiment, the second display unit 232 may output operational information by displaying an image indicating the operational information of the gantry 210 on an image 500 of the gantry 210.

Figure 5A:
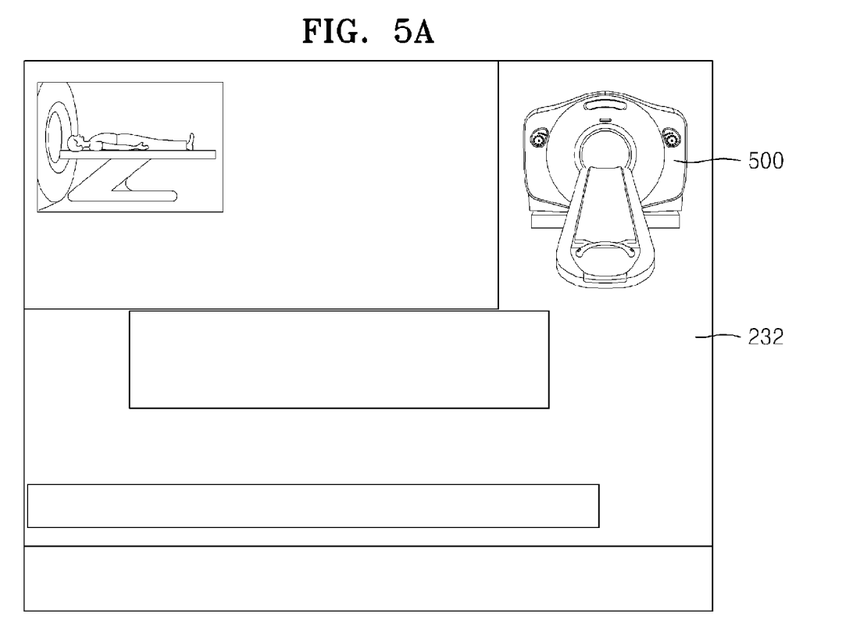
FIGS. 5A to 5D schematically illustrate a second display unit graphically displaying the operational information of a gantry, according to an embodiment of the present invention.

FIG. 5A illustrates that the gantry 210 of the medical imaging apparatus 200 is in a scanning standby state. According to the present embodiment, when the gantry 210 is in a scanning standby state, the second display unit 232 may output an image including the image 500 of the gantry 210 displayed in white.

Figure 5B:
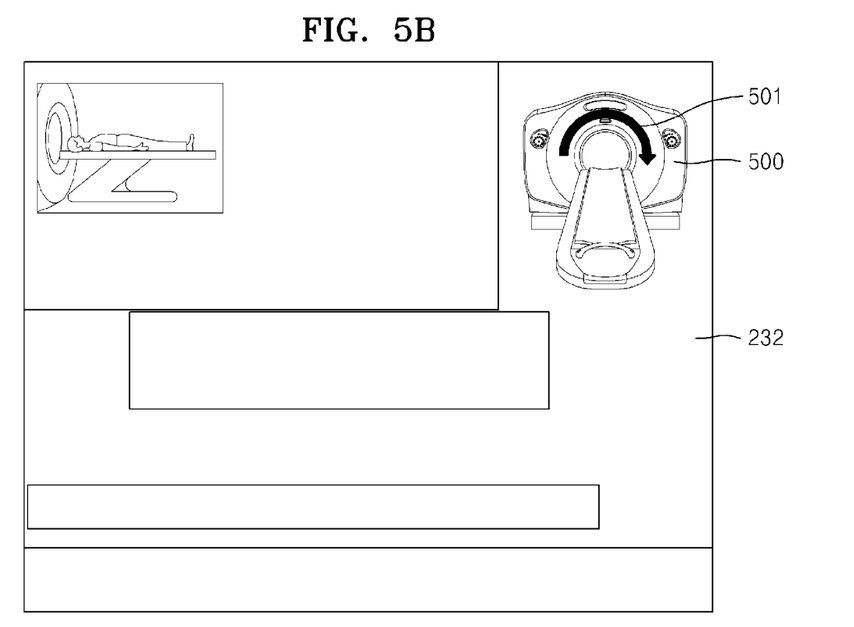

As illustrated in FIG. 5B, the medical imaging apparatus 200 performs a scanning operation and thus the source 211 and the detector 212 are rotated clockwise. The second display unit 232 may display the rotational direction of the source 211 and the detector 212 by using an arrow 501 on the image 500 of the gantry 210.

Figure 5C:
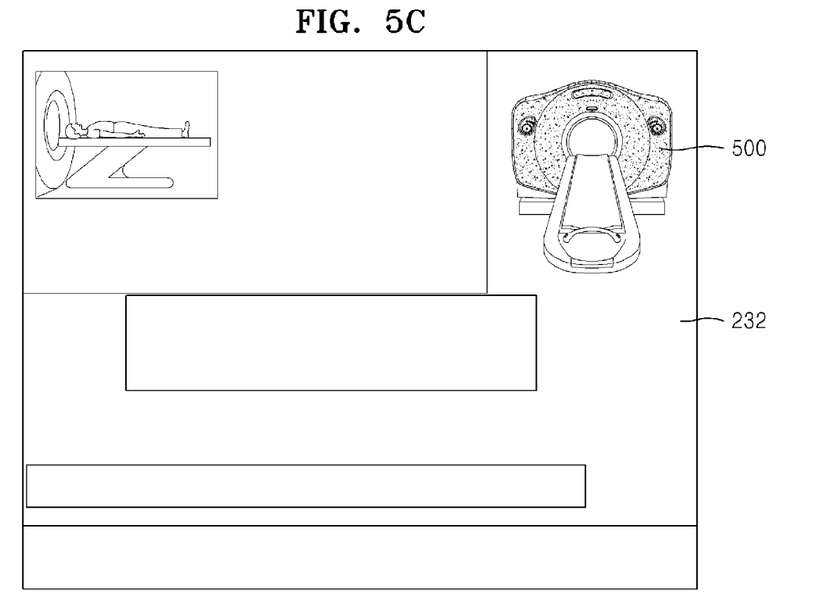

FIG. 5C illustrates that the gantry 210 is in a scanning preparation state. When the gantry 210 is in a scanning preparation state, the second display unit 232 may output an image including the image 500 of the gantry 210 displayed in green.

Figure 5D:
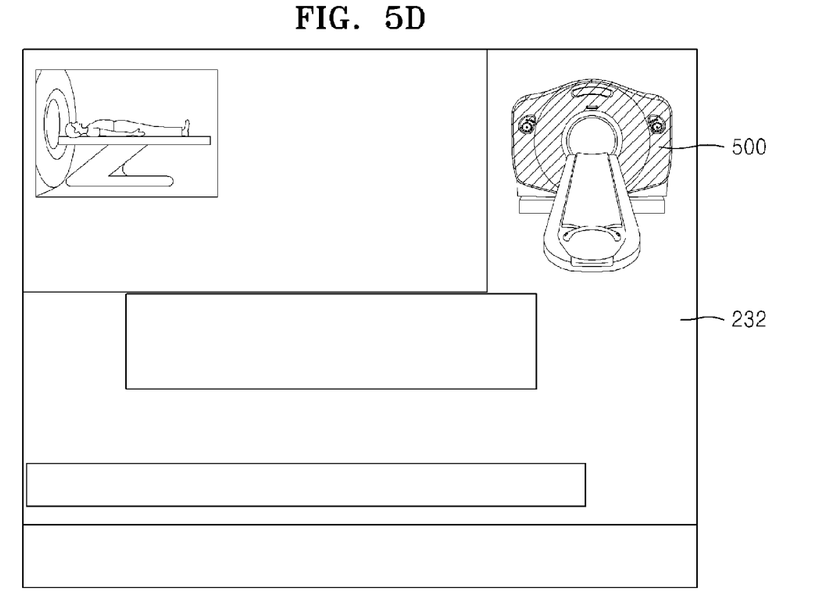

FIG. 5D illustrates that the gantry 210 is in a scanning-on state. When the gantry 210 is in a scanning-on state, the second display unit 232 may output an image including the image 500 of the gantry 210 displayed in red.

As illustrated in FIGS. 5A to 5D, according to the present embodiment, the second display unit may display the state of the gantry 210, for example, a scanning preparation state or a scanning-on state, by changing the color of the image 500 of the gantry 210. Also, the second display unit 232 may indicate that the source 211 and the detector 212 are rotated in a predetermined direction by displaying the arrow 501 on the image 500 of the gantry 210.

Figure 6:
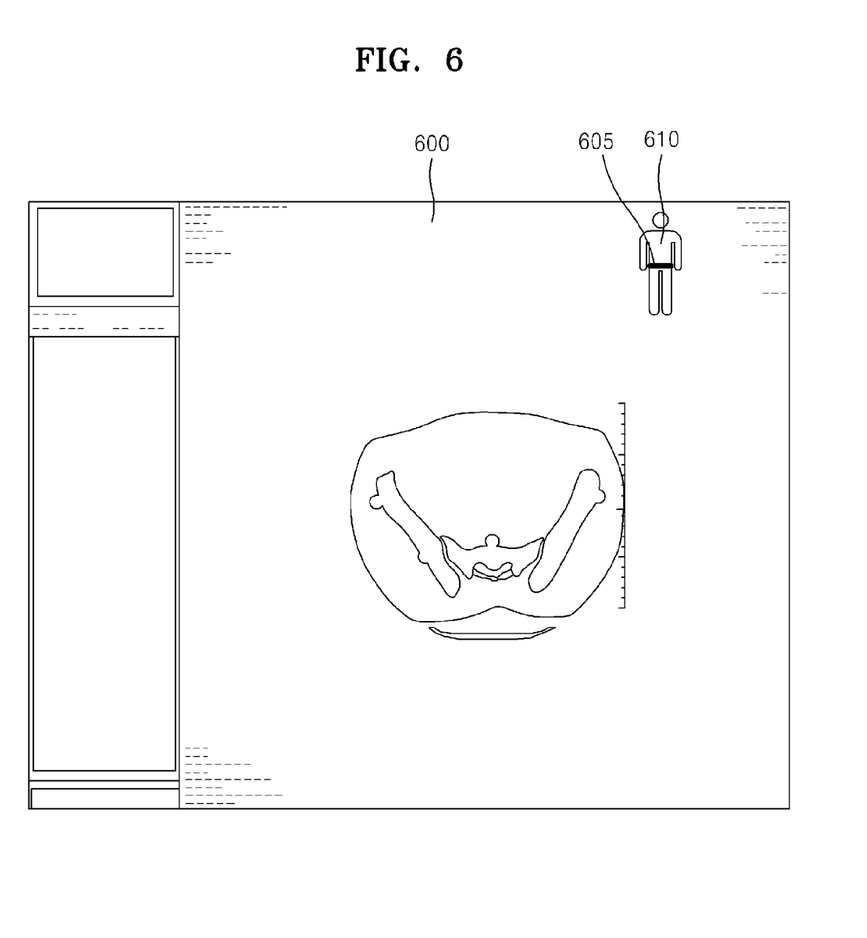
FIG. 6 schematically illustrates the second display unit displaying a body marker, according to an embodiment of the present invention.

FIG. 6 schematically illustrates the second display unit 232 displaying a body marker, according to an embodiment of the present invention. As illustrated in FIG. 6, the second display unit 232 may output a CT image 600 scanning the pelvis. Also, the second display unit 232 may output the CT image 600 and a body marker 610 corresponding to the CT image 600. The body marker 610 may be an image of a human on which a position 605 corresponding to the pelvis is marked. It is understood that the body marker 610 may further include in a form of a text.

As described above, the medical imaging apparatus according to the present invention facilitates identification of the operational information of a gantry included in the medical imaging apparatus.

The medical imaging apparatus and methods according to the above-described example embodiments may use one or more processors, which may include a microprocessor, central processing unit (CPU), digital signal processor (DSP), or application-specific integrated circuit (ASIC), as well as portions or combinations of these and other processing devices.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

The method for controlling an x-ray imaging apparatus according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations of the above-described embodiments, or vice versa. The program instructions may be executed by one or more processors. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

While this invention has been particularly shown and described with reference to exemplary embodiments thereof, it will be understood by those of ordinary skill in the art that various changes in form and details may be made therein without departing from the spirit and scope of the invention as defined by the appended claims.

What is claimed is:

1. A medical imaging apparatus comprising:
a gantry comprising an opening portion for accommodating an object in the center of the gantry, a source for irradiating an X-ray toward the opening portion and a detector for detecting the X-ray passing through the object, wherein the gantry allows the source and the detector to rotate around the object;
a control unit for obtaining operational information of the gantry; and
a display unit for outputting the obtained operational information of the gantry to a user outside of the gantry,
wherein the display unit comprises a first display unit which is provided on an outer surface of the gantry and surrounds an entrance of the opening portion through which the object is accommodated into the opening portion.

2. The medical imaging apparatus of claim 1, wherein the operational information of the gantry includes at least one of scanning operation information indicating whether the gantry is performing a scanning operation, rotational information regarding at least one of the source and the detector, malfunction information indicating whether the gantry is operating normally, and positional information regarding at least one of the source and the detector in the gantry.

3. The medical imaging apparatus of claim 2, wherein the rotational information includes at least one of a rotational speed and a rotational direction.

4. The medical imaging apparatus of claim 1, wherein the first display unit comprises a light emitting diodes display (LED display).

5. The medical imaging apparatus of claim 4, wherein the first display unit comprises an LED display that is circularly provided on an outer surface of the gantry.

6. The medical imaging apparatus of claim 4, wherein the first display unit indicates the operational information of the gantry by changing colors of the LEDs display.

7. The medical imaging apparatus of claim 1, wherein the display unit further comprises a second display unit for outputting the operational information in a form of an image.

8. The medical imaging apparatus of claim 7, wherein the second display unit displays the operational information on an image of the gantry.

9. The medical imaging apparatus of claim 8, wherein the second display unit displays rotational information regarding at least one of the source and the detector on the image of the gantry by using an arrow.

10. The medical imaging apparatus of claim 8, wherein the second display unit displays scanning operation information of the gantry on the image of the gantry by using colors.

11. The medical imaging apparatus of claim 7, wherein the second display unit further outputs a computerized tomography (CT) image of the object and a body marker corresponding to the CT image of the object.

12. A method of providing operational information of a gantry included in a medical imaging apparatus, the method comprising:
driving the gantry to allow a source and a detector included in the gantry to rotate around an object, wherein the gantry comprising an opening portion for accommodating an object in the center of the gantry, the source for irradiating an X-ray toward the opening portion and the detector for detecting the X-ray passing through the object;
obtaining the operational information of the gantry; and
displaying the obtained operational information of the gantry to a user outside of the gantry,
wherein the displaying of the obtained operational information comprises displaying the obtained operational information by using a first display unit which is provided on an outer surface of the gantry and surrounds an entrance of the opening portion through which the object is accommodated into the opening portion.

13. The method of claim 12, wherein the operational information of the gantry includes at least one of scanning operation information indicating whether the gantry is performing a scanning operation, rotational information regarding at least one of the source and the detector, malfunction information indicating whether the gantry is operating normally, and positional information regarding at least one of the source and the detector in the gantry.

14. The method of claim 13, wherein the rotational information includes at least one of a rotational speed and a rotational direction of the gantry.

15. The method of claim 12, wherein the first display unit comprises an LED display.

16. The method of claim 15, wherein the displaying of the obtained operational information of the gantry by using the first display unit comprises displaying the obtained operational information of the gantry by using an LED display that is circularly provided on an outer surface of the gantry.

17. The method of claim 15, wherein the displaying of the obtained operational information of the gantry by using the first display unit comprises displaying the obtained operational information of the gantry by changing colors of the LEDs display.

18. The method of claim 12, wherein the displaying of the obtained operational information of the gantry further comprises displaying the operational information as an image.

19. The method of claim 18, wherein the displaying of the obtained operational information in the image comprises displaying the operational information on an image of the gantry.

20. The method of claim 19, wherein the displaying of the obtained operational information in the image comprises displaying rotational information regarding at least one of the source and the detector on the image of the gantry by using an arrow.

21. The method of claim 19, wherein the displaying of the operational information in an image comprises displaying scanning operation information of the gantry on the image of the gantry by using colors.

22. The method of claim 18, wherein the displaying of the operational information in the image further comprises displaying a computerized tomography (CT) image of the object and a body marker corresponding to the CT image of the object.

* * * * *

UNITED STATES PATENT AND TRADEMARK OFFICE
CERTIFICATE OF CORRECTION

| | | |
|---|---|---|
| PATENT NO. | : 9,179,877 B2 | Page 1 of 1 |
| APPLICATION NO. | : 13/937886 | |
| DATED | : November 10, 2015 | |
| INVENTOR(S) | : Eung-jun Youn et al. | |

It is certified that error appears in the above-identified patent and that said Letters Patent is hereby corrected as shown below:

On The Title Page, Item 73

First Page
Column 1 (Assignee), Line 2:
Delete "Suwon-Si (KR)" and insert -- Suwon-si (KR) --, therefor.

In The Claims

Claim 4, Column 9, Line 57:
Delete "diodes" and insert -- diode --, therefor.

Claim 6, Column 9, Line 64:
Delete "LEDs" and insert -- LED --, therefor.

Claim 17, Column 10, Line 56:
Delete "LEDs" and insert -- LED --, therefor.

Signed and Sealed this
Nineteenth Day of April, 2016

Michelle K. Lee
*Director of the United States Patent and Trademark Office*